United States Patent
Moussavi et al.

(10) Patent No.: US 7,559,903 B2
(45) Date of Patent: Jul. 14, 2009

(54) BREATHING SOUND ANALYSIS FOR DETECTION OF SLEEP APNEA/POPNEA EVENTS

(75) Inventors: Zahra Moussavi, Winnipeg (CA); Azadeh Yadollahi, Winnipeg (CA); Sergio Camorlinga, Winnepeg (CA)

(73) Assignee: TR Technologies Inc., Edmonton, Alberta (CA)

( * ) Notice: Subject to any disclaimer, the term of this patent is extended or adjusted under 35 U.S.C. 154(b) by 34 days.

(21) Appl. No.: 11/692,729

(22) Filed: Mar. 28, 2007

(65) Prior Publication Data

US 2008/0243014 A1 Oct. 2, 2008

(51) Int. Cl.
 *A61B 5/08* (2006.01)
 *A61B 7/00* (2006.01)
(52) U.S. Cl. .................. 600/538; 600/529; 600/586
(58) Field of Classification Search ......... 600/529–543, 600/586
 See application file for complete search history.

(56) References Cited

U.S. PATENT DOCUMENTS

| | | | | |
|---|---|---|---|---|
| 5,123,425 A | * | 6/1992 | Shannon et al. | 128/848 |
| 5,265,624 A | * | 11/1993 | Bowman | 128/848 |
| 5,275,159 A | * | 1/1994 | Griebel | 600/324 |
| 5,797,852 A | * | 8/1998 | Karakasoglu et al. | 600/529 |
| 5,844,996 A | | 12/1998 | Enxmann et al. | |
| 6,120,441 A | * | 9/2000 | Griebel | 600/300 |
| 6,171,258 B1 | * | 1/2001 | Karakasoglu et al. | 600/529 |
| 6,213,955 B1 | * | 4/2001 | Karakasoglu et al. | 600/529 |
| 6,241,683 B1 | | 6/2001 | Macklem | |
| 6,290,654 B1 | * | 9/2001 | Karakasoglu | 600/529 |
| 6,415,033 B1 | * | 7/2002 | Halleck et al. | 381/67 |
| 6,517,497 B2 | * | 2/2003 | Rymut et al. | 600/538 |
| 6,575,916 B2 | * | 6/2003 | Halleck et al. | 600/528 |
| 6,666,830 B1 | * | 12/2003 | Lehrman et al. | 600/586 |
| 6,706,002 B1 | * | 3/2004 | Halleck et al. | 600/586 |
| 6,935,335 B1 | * | 8/2005 | Lehrman et al. | 600/529 |
| 6,947,565 B2 | * | 9/2005 | Halleck et al. | 381/67 |
| 2002/0072685 A1 | * | 6/2002 | Rymut et al. | 600/529 |
| 2005/0197588 A1 | | 9/2005 | Freeberg | |
| 2005/0288728 A1 | | 12/2005 | Libbus et al. | |
| 2007/0118054 A1 | | 5/2007 | Pinhas et al. | |

* cited by examiner

*Primary Examiner*—Robert L Nasser
*Assistant Examiner*—Navin Natnithithadha
(74) *Attorney, Agent, or Firm*—Adrian D. Battison; Ade & Company Inc.

(57) ABSTRACT

Apparatus for use detection of apnea includes a microphone mounted in the ear of the patient for detecting breathing sounds and a second external microphone together with an oximetric sensor. A transmitter at the patient compresses and transmits the signals to a remote location where there is provided a detector module for receiving and analyzing the signals to extract data relating to the breathing. The detector uses the entropy or range of the signal to generate an estimate of air flow while extracting extraneous snoring and heart sounds and to analyze the estimate of air flow using Otsu's threshold to detect periods of apnea and/or hypopnea. A display provides data of the detected apnea/hypopnea episodes and related information for a clinician.

23 Claims, 4 Drawing Sheets

BREATHING SOUND ANALYSIS FOR DETECTION OF SLEEP APNEA/POPNEA EVENTS

This invention relates to an apparatus for use in breathing sound analysis for detection of sleep apnea/hypopnea events.

This application is related to a co-pending Application filed on the same day as this application under Ser. No. 11/692,745 and entitled BREATHING SOUND ANALYSIS FOR ESTIMATION OF AIRFLOW RATE

BACKGROUND OF THE INVENTION

Sleep apnea syndrome (SAS) is a common respiratory disorder. By definition, apnea is the cessation of airflow to the lungs (usually during sleep) which lasts for at least 10 seconds. Polysomnography (PSG) during the entire night is currently the only reliable diagnostic method of sleep apnea. The standard PSG consists of recording various physiological parameters including EEG, ECG, EMG of chins and legs, nasal airflow, electro-oculogram (EOG), abdominal and thoracic movements, and blood oxygen saturation (SaO2). However, the high cost of the system, discomfort of the electrodes connecting to the body and the high amount of information required to be analyzed are the main disadvantages of this method.

Several researchers have tried to detect apnea using smaller number of features such as airflow, SaO2 and respiratory effort. Also, in a recent study an acoustical method based on lung sounds power at different frequency ranges was proposed for apnea and snore detection with a sensitivity of about 77% at best situation. In the other studies airflow was measured using either face masks or nasal cannulae and its cessation was detected as the main sign of apnea. However, face mask results in unavoidable changes in breathing pattern and also its application is a challenge when studying children with neurological impairments. On the other hand, usage of nasal cannulae is highly questionable due to the leakage of airflow and possibility of breathing through the mouth.

Sleep apnea syndrome (SAS) can become very serious. It is most common in obese people, people with high blood pressure, people with narrowed airway due to tonsils or adenoids, people with stroke or brain injuries, and smokers. Sleep apnea occurs two to three times more often in the elderly and also more in males than in females. It can cause cardiovascular problems, daytime fatigue, irritability, lack of concentration and sleepiness causing accidents. Most people with obstructive sleep apnea snore; but not everybody that snores has sleep apnea.

Analysis of breathing sounds from a patient for determination of sleep apnea and/or hypopnea is proposed in a paper entitled "Validation of a New System of Tracheal sound Analysis for the diagnosis of Sleep Apnea-Hypopnea Syndrome" by Nakano et al in "SLEEP" Vol 27 No. 5 published in 2004. This constitutes a research paper postulating that sleep apnea can be detected by breathing sound analysis but providing no practical details for a system which may be used in practise. It is believed that no further work has been published and no commercial machine has arisen from this paper.

U.S. Pat. No. 6,290,654 (Karakasoglu) issued Sep. 18, 2001 discloses an apparatus for analyzing sounds to estimate airflow for the purposes of detecting apnea events. It then uses a pattern recognition circuitry to detect patterns indicative of an upcoming apnea event. In this patent two microphones located close to the patients face and on patient's trachea are used to record respiratory sounds and ambient noise, respectively. The third sensor records oxygen saturation. Two methods based on adaptive filter were applied to remove the ambient noise from respiratory sounds. Then the signal was bandpass filtered and used for airflow estimation. The estimated airflow signals from two sensors and oxygen saturation data were fed to a wavelet filter to extract respiratory features. Then the extracted features along with the logarithm values of the estimated airflow, signals from two sensors and oxygen saturation sensor were applied to a neural network to find normal and abnormal respiratory patterns. In the next step k-mans classifier was used to find apnea and hypopnea events in the abnormal respiratory patterns. In this patent after removing background noise from the signals, the signals are fed to a filter bank which consists of a series of filters in the range of 3001500 with bandwidth of 100 Hz and then the output of the filter with higher signal to noise ration is selected for flow estimation. Respiratory sounds data below 300 Hz are crucial for flow estimation during shallow breathing which occurs during sleep. Finally in this patent both acoustical signals and oxygen saturation data are used for apnea detection, In U.S. Pat. No. 5.797,852 (Karakasoglu) assigned to Local Silence Inc filed 1993 and issued 1998 and now expired is disclosed an apparatus for detecting sleep apnea using a first microphone for detection of breathing sounds and a second microphone for cancelling ambient sounds. This patent apparently lead to release of a machine called "Silent Night" which was approved by FDA in 1997 but apparently is no longer available. In this patent a system comprised of two microphones is proposed for apnea detection. The first microphone is placed near the nose and mouth of the subject to record inhaling and exhaling sounds and the second microphone is positioned in the air near the patient to record ambient noise. The data of the second microphone is used to remove ambient noise from the first signal by means of adaptive filtering. Then the filtered signal is applied to a model for estimating flow and classifying as apnea or normal breathing. The way the patent proposes to record signals it is obvious that the author has never done any experiment with the respiratory sounds. In this patent the main signal is recorded from a place "near" mouth and nose. This is a very vague description of the microphone location and will not record any respiratory sounds especially at low flow rates, which is the rate during sleep usually.

A related U.S. Pat. No. 5,844,996 (Enzmann and Karakasoglu) issued 1998 to Sleep Solutions Inc is directed to reducing snoring sounds by counteracting the sounds with negative sounds. This Assignee has a sleep apnea detection system currently on sale called NovaSom QSG but this uses sensors of a conventional nature and does not attempt to analyze breathing sounds. In this patent a method for removing snoring sounds is proposed. The patent consists of two microphones and a speaker. The first microphone is placed near the noise source to record the noise. The recorded noise is analyzed to generate a signal with opposite amplitude and sign and played by the speaker to neutralize noise in the second position. In order to decrease the error, the second microphone is placed in the second position to get the overall signal and noise and compensate for the noise. This patent is about noise cancellation and specially snoring sound, not apnea detection or screening. The first microphone which provides the primary signal is placed near the head of the subject and not in a place suitable for recording respiratory sounds. Nothing is done for flow estimation or apnea detection.

U.S. Pat. No. 6,241,683 (Macklem) issued Jun. 5, 2001 discloses a method for estimating air flow from breathing sounds where the system determines times when sounds are too low to make an accurate determination and uses an interpolation method to fill in the information in these times. Such an arrangement is of course of no value in detecting apnea or hypopnea since it accepts that the information in these times is inaccurate. In this patent tracheal sound is used for estimation of flow ventilation parameters. Although they mentioned their method can be used to detect several respiratory diseases including sleep apnea, their main focus is not on the sleep apnea detection by acoustical means. They do not mention how they are going to remove ambient noise and snoring sounds from the recordings nor the use of oxygen saturation data for further investigations. Also they have used wired microphone placed over trachea. The other difference is in the signal processing method applied for flow estimation. They are using average power of tracheal sound for flow estimation but it has been shown that average power can not follow flow changes accurately. Also in this study the recorded respiratory sounds are bandpass filtered in the range of [200-1000]Hz to remove heart sounds, which results in low accuracy in estimating flow during shallow breathing.

U.S. Pat. No. 6,666,830 (Lehrman) issued Dec. 23, 2003 discloses an apparatus for analyzing sounds to detect patterns indicative of an upcoming apnea event. It does not attempt to determine an estimate of air flow to actually locate an apnea event but instead attempts to detect changes in sound caused by changes in airflow patterns through the air passages of the patient. In this patent four microphones are located on a collar around the neck to measure respiratory sounds and a sensor is placed close to nostrils to measure airflow. The airflow signal is used to find breathing pattern and the microphones signals are filtered and analyzed to find the onset of apnea event. In this patent snoring and ambient noise detection has not been discussed. This arrangement does not estimate flow from respiratory sounds so that they cannot calculate respiratory parameters such as respiratory volume based on flow data.

Polysomnography (PSG) testing during the entire night is currently the accepted gold standard diagnostic method of sleep apnea. The standard PSG consists of recording various physiological parameters including EEG, ECG, EMG of chins and legs, nasal airflow, electro-oculogram (EOG), abdominal and thoracic movements, and blood oxygen saturation (SaO2) and usually snoring sounds. However, the high cost of the system, discomfort of the electrodes connecting to the body and the high amount of information required to be analyzed are the major disadvantages of this testing method.

This complexity of the monitoring system causes a very long waiting list for patients to go through a sleep study. Hence healthcare providers and payers are seeking alternative methods, portable devices and automated/intelligent systems in which sleep apnea testing can be done at the home of patient but with the same diagnostic values.

SUMMARY OF THE INVENTION

It is one object of the invention to provide an apparatus for use in breathing sound analysis for detection of sleep apnea/hypopnea events.

According to the invention there is provided an apparatus for use in use in analysis of breathing of a patient during sleep for detection of apnea comprising:

a microphone arranged to be located on the patient for detecting breathing sounds;

a transmitter at the patient for transmitting signals from the breathing sounds to a remote location;

a detector module for receiving and analyzing the signals to extract data relating to the breathing;

the detector module being arranged to analyze the signals to generate an estimate of air flow while extracting extraneous sounds related to snoring and/or heart;

the detector module being arranged to analyze the estimate of air flow to detect periods of apnea and/or hypopnea;

and a display of the detected apnea/hypopnea episodes and related information for a clinician.

Preferably there is provided additionally a microphone to collect extraneous sounds from the patient and a sensor for oximetric signals for transmission to the remote receiver.

Preferably the transmitter is arranged to compress data for transmission.

Preferably the remote receiver and detector module are arranged to receive signals from a plurality of transmitters at different locations through an organizer module.

Preferably the detector module connects to an interface for transmission of data to different locations.

Preferably there is provided a second microphone arranged to receive sounds from the patient in the vicinity of the patient so as to be sensitive to snoring and wherein the detector module is arranged to use adaptive filtering to extract the signals relating to the snoring from the signals including both the breathing sounds and the snoring sounds.

Preferably the detector module is arranged to cancel heart sounds.

Preferably the detector module is arranged to calculate a function representing the range of the signal or the entropy of the signal providing an estimate of air flow during breathing.

Preferably the detector module is arranged to cancel heart sounds from the function. In one preferred method, the function is the range of the signal which is defined as the log of the difference between minimum and maximum of the signal within each short window (i.e. 100 ms) of data.

In another preferred method, the function is the entropy of the signal which is defined by the following formula:

$$H(p) = \sum_{i=1}^{N} p_i \log p_i,$$

where $p_i$ is the probability distribution function of the $i^{th}$ event.

Preferably sleep apnea and/or hypopnea is detected by comparing the function to a threshold of estimated air flow.

Preferably the threshold is defined as the minimum of the Otsu's threshold and the average value of the function within each data window where the Otsu's threshold is defined as the threshold which maximizes the between class variance.

Preferably the display includes a display of airflow versus time is plotted with apnea and hypopnea episodes marked in.

Preferably the display includes oximetry data plotted in association with the estimated airflow.

Preferably the display is capable of zoom-in and zoom-out functions in the same window for both airflow and oximetry data simultaneously.

Preferably the display is capable of playing the breathing and snoring sounds in any zoomed-in or zoomed-out data window.

Preferably the display is capable of playing the breathing and snoring sounds in any zoomed-in or zoomed-out data window.

Preferably the display is capable of displaying the extracted information about the frequency and duration of apnea/hypopnea episodes, and their association with the level of oximetry data in a separate window for the clinician.

Preferably the microphone is arranged to be located in the ear of the patient.

Preferably the microphone in the ear includes a transmitter arranged for wireless transmission to a receiver.

The apparatus described hereinafter uses tracheal sound entropy to detect apnea occurrence during breathing.

The apparatus described hereinafter provides an integrated system to acquire, de-noise, analyze the tracheal respiratory sounds, estimate airflow acoustically, detect apnea episodes, report the duration and frequency of apnea, and to use wireless technology to transfer data to a remote clinical diagnostic center.

In the present invention the sounds are recorded from inside the ear. In this patent the snore detection, air volume estimation, difference between apnea and hypopnea and recording of oximetry data as a complementary data were not considered, while in our study they are. The flow estimation method is also different. The most important difference in relation to the present invention is that the microphone and oxygen saturation sensors are wireless and very light, which increase the mobility of the subject and minimizes the inference of data recording process and patient's sleeping In the present invention the main sensor for recording respiratory sounds is located on the trachea or inside the ear which has been found the best location for flow estimation purposes while in this patent respiratory sounds are recorded with a sensor positioned near patients face. Also the present sensors are wireless sensors which decrease the movement noises and produce less interference when subject is asleep.

Such a system reduces the need for polysomnography tests, hence reducing the long waiting list for an accurate diagnostic assessment. The apparatus described hereinafter also facilitates studying patients with mobility or behavioral cognitive issues.

Long distance monitoring and diagnostic aid tools provide large financial saving to both the health care system and families. The apparatus described hereinafter provides a novel system to both developing a new and yet simple diagnostic tool for sleep apnea disorder, and also a new way to connect the specialists and physicians with patients either in remote areas or even at their homes. Aside from its obvious benefit for covering the remote areas with equal opportunity for health care, it also reduces the long waiting list for sleep studies. From a public health perspective non-invasive and inexpensive methods to determine airway responses across all ages and conditions present a major step forward in the management of sleep apnea disorders.

The apparatus described hereinafter provides a portable and wireless medical monitoring device/intelligent diagnostic system that enables clinicians to remotely and accurately diagnose sleep apnea at much less cost and which greatly reduces discomfort and inconvenience to the patient.

The apparatus described hereinafter can pave the way for a new line of research and application that will simplify the measurement techniques to a large degree while enhancing the quality of symptomatic signs of the disease detection and helping an objective diagnosis.

The apparatus described hereinafter provides a novel, integrated diagnostic system to wirelessly acquire, de-noise, analyze tracheal respiratory sounds, estimate airflow acoustically, detect sleep apnea episodes, report the duration and frequency of apnea and use secure Internet-based networking technologies to transfer data to a remote centralized clinical diagnostic center.

BRIEF DESCRIPTION OF THE DRAWINGS

One embodiment of the invention will now be described in conjunction with the accompanying drawings in which;

FIG. 3($b$) is a graphical representation of entropy after applying nonlinear median filter (star marks represents the estimated apnea segments)

FIG. 3($c$) is a graphical representation of flow signal (solid line) along with the estimated (dotted line) and real (dashed line) apnea segments for a typical subject.

DETAILED DESCRIPTION

One of the reasons to record many signals in a sleep study is the inaccuracy of those recorded signals in sleep apnea detection when they are used as a single measure. For example, nasal cannulae are used to measure airflow, however, when the patient breathes through the mouth, the nasal cannulae register nothing and hence give a false positive detection error for apnea. Therefore, combination of nasal pressure plus thermistor and End-tidal carbon dioxide concentration in the expired air ($ETCO_2$) is used to have a qualitative measure of respiratory airflow. The abdominal movement recordings are mainly used to detect respiratory effort and hence to distinguish between central and obstructive sleep apnea. The ECG signals are also being used for detecting heart rate variability and another measure for apnea detection as well as monitoring patient's heart condition during the night. The combination of EOG (Electrooculogram), EEG (Electroencephalogram), and EMG (Electromyogram) signals are used for assessing the rapid eye movement (REM) sleep stage that is characterized by desynchronization of the EEG and loss of muscle tone. Recording these signals are necessary if insight in sleep quality is sought for diagnosis of certain sleep disorders. The most important information that doctors seek from a complete sleep study is the duration and frequency of apnea and/or hypopnea and the blood's Oxygen saturation ($SaO_2$) level of the patient during the apnea. Oxygen level usually drops during the apnea and will rise quickly with awakenings. However, oximetry alone does not detect all cases of sleep apnea.

As the first and most important information of a sleep study is an accurate measure of duration and frequency of apnea during sleep, the present arrangement provides a fully automated system to detect apnea with only one single sensor that can also easily be applied by the patient at home and detect apnea acoustically; hence reducing the need for a complete laboratory sleep study.

The apparatus provides an integrated system for remote and local monitoring and assessment of sleep apnea as a diagnostic aid for physicians and allows the following:

To record the $SaO_2$ data simultaneously with respiratory sound signals through either a neck band with a microphone mounted in a chamber placed over the supra-sternal notch, or by a microphone from inside the ear, followed by a signal conditioning unit.

To screen the raw data, separate snoring and other adventitious sounds from breath sounds, estimate flow from the sounds and detect apnea and/or hypopnea episodes, determine the duration and frequency of the apnea episodes and finally display the raw data, estimated airflow and display the estimated airflow with marked detected apnea/hypopnea along with related information (duration, frequency and the corresponded $SaO_2$ data).

Figure 1:
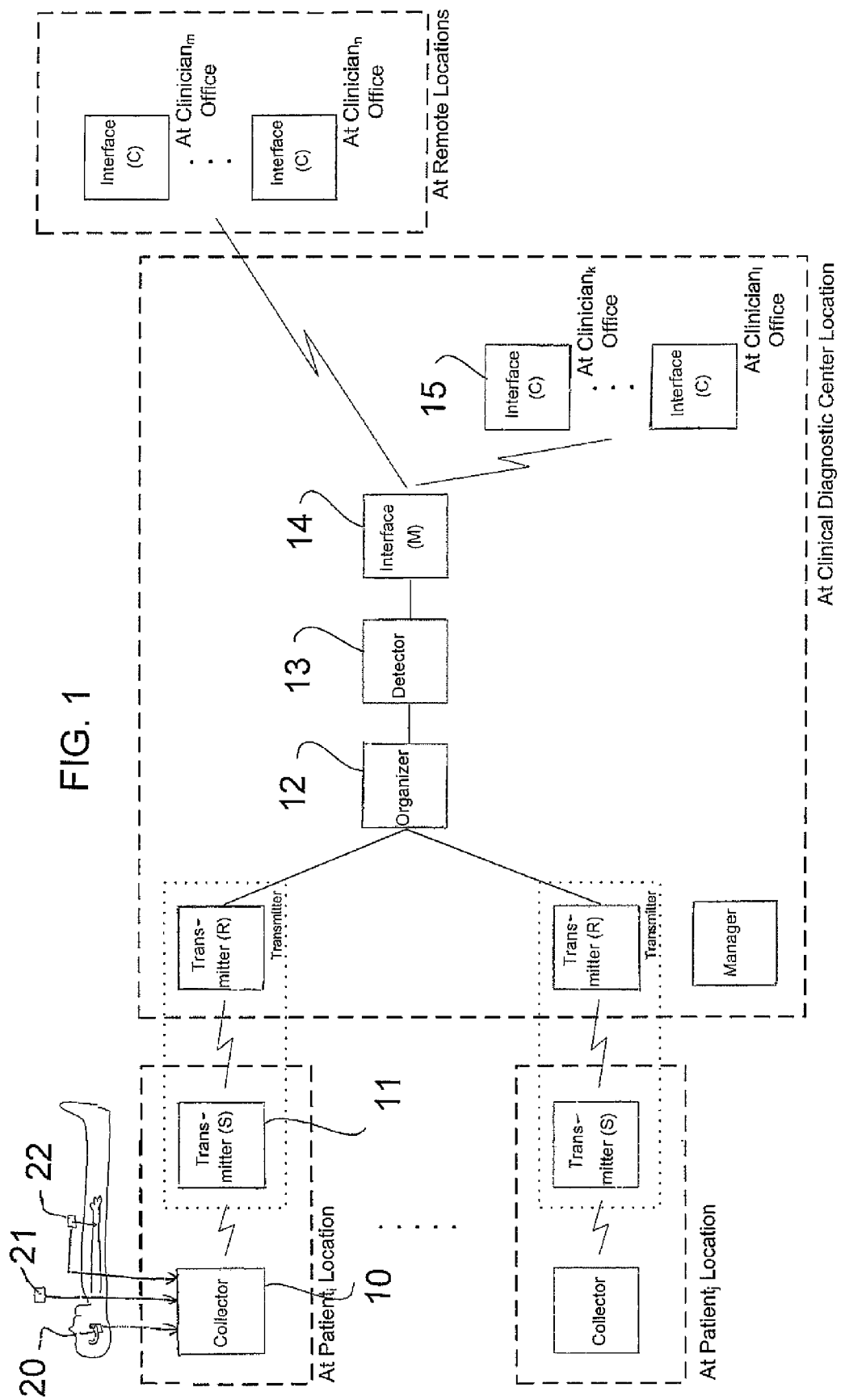
FIG. 1 is a schematic illustration of a sleep apnea detection apparatus according to the present invention.
Figure 2:
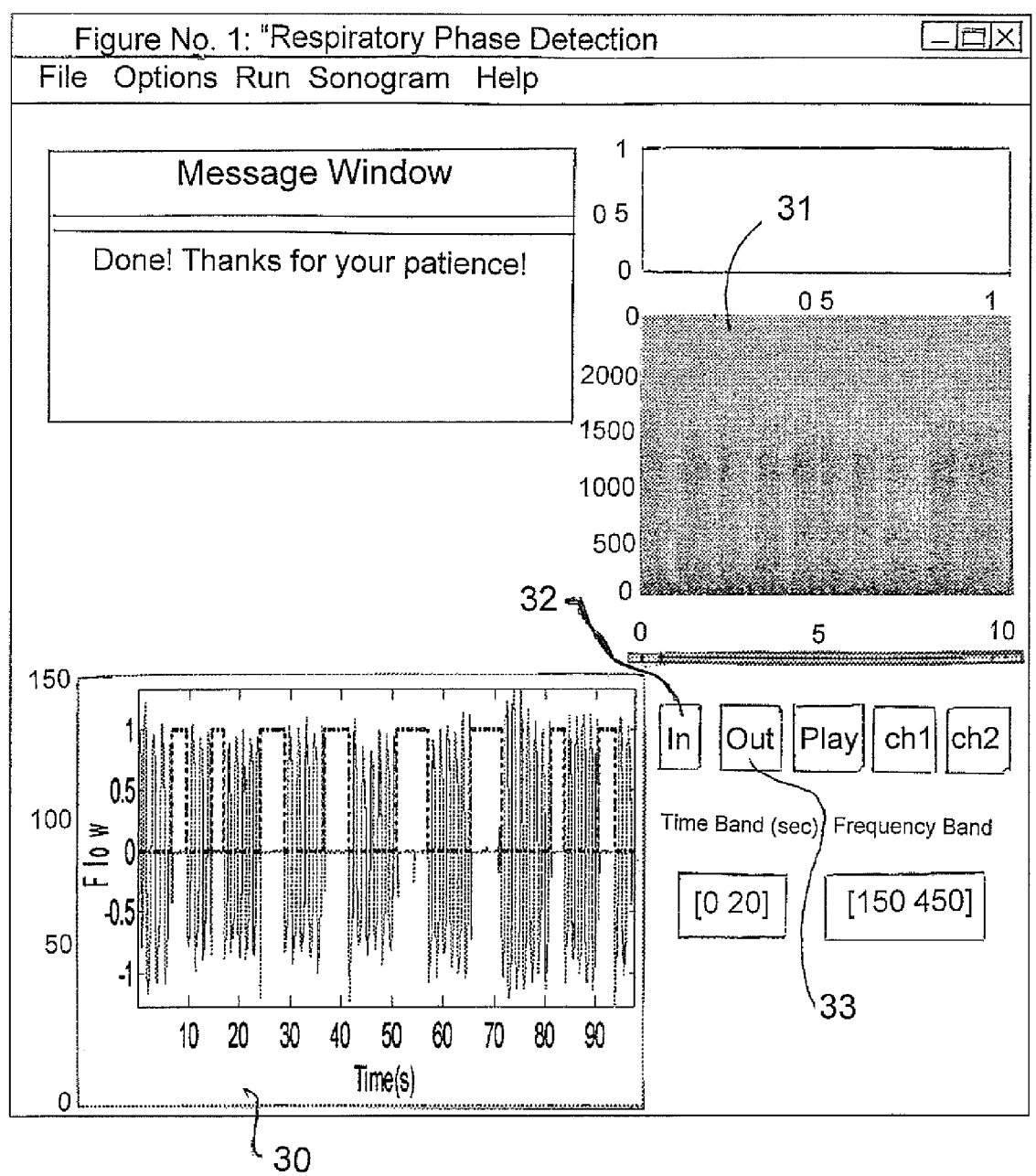
FIG. 2 is an illustration of a typical screen displaying the data to the physician.

FIG. 1 shows the apparatus for sleep apnea detection that can also be used as a home-care device while being connected to a clinical diagnostic center for online monitoring.

From a public health perspective, non-invasive and inexpensive methods to determine airway responses across all ages and conditions would present a major step forward in the management of sleep apnea disorders The apparatus consists of six modules that permit sleep apnea detection diagnosis. The clinical diagnosis can be performed either locally (e.g. at a clinical diagnostic center) and/or remotely (e.g. at clinician's office/home). The apparatus will support several clinicians simultaneously carrying out clinical work on different patients. Likewise, patients can be monitored either locally (e.g. at a clinical diagnostic center) and/or remotely (e.g. at patient's home). The apparatus will also support many patients being concurrently monitored.

The apparatus has the following modules
Collector module 10,
Transmitter module 11,
Organizer module 12,
Detector module 13,
Interface module 14, and
Manager module 15.

Collector module 10 captures physiological signals from different body parts. The body parts include a microphone and transmitter 20 at the ear or over the neck by a wireless microphone mounted in chamber with a neckband for recording sounds, a sensor 22 at the fingers of the patient for recording oximetry data and an external microphone 21 for recording sound from the environment around the patient. Other signals can be detected in some cases from other body parts if the physicians request other biological signals, but this is not generally intended herein. The collector module locally transfers wirelessly the signals to the Transmitter module 11.

Transmitter module 11 receives biological signals from the Collector module 10, securely transmits those signals and receives the signals at the diagnostic center for its delivery to the Organizer module 12.

The Transmitter module 11 consists of two components: The Transmitter Sender (S) and the Transmitter Receiver (R). The Transmitter Sender together with the Collector module resides at the patient location. The Transmitter Sender receives and store temporally signals from the Collector, and securely and reliably transfers the signals to the Transmitter Receiver. The Transmitter Receiver resides at the diagnostic center location. The Transmitter Receiver securely and reliably accepts the signals from the Transmitter Sender, and forwards the signals to the Organizer for the signal management and processing. There is one pair of collector-transmitter modules per patient being monitored.

Inter-Transmitter components signal transmission can occurred locally for those cases when the Collector-Transmitter Sender resides in the same center (e.g. at a diagnostic facility) or remotely for those cases when the Collector-Transmitter Sender resides externally (e.g. at a patient home). The transmission can be wireless or wired (e.g. through the internet/intranet).

Organizer module 12 receives all captured signals from the Transmitter module, organizes and classifies received signals per patient/physician and prepares the signals for its processing by the Detector module. The Organizer module simultaneously supports receiving many signals from different patients that is signals from collector-transmitter module pairs.

Detector module 13 pre-processes and analyzes the patient biological signals, and performs the sleep apnea detection. The Detector performs snoring sound detection and separation prior to the apnea/hypopnea detection. The Detector has self-calibrated acoustical respiratory airflow estimation and phase detection utilized in respiratory and sleep apnea assessments.

Interface module 14 provides the graphical user interface to the clinicians. The Interface module gives a secure, reliable, user-friendly, interactive access to the analysis performed by the Detector and it is organized per patient/physician. The Interface module consists of two main components: the Interface Master (M) and the Interface Client (C). The Interface Master serves the information to the Interface Client(s), while the Interface Client provides the access to the clinicians. Several Interface Clients can run concurrently giving out results to several clinicians. The Interface Client can be executed locally (e.g. intranet) or externally (e.g. internet).

Manager module 15 provides the application management functions. It provides the graphical user interface to the application administrator at the diagnostic center location.

All system/application parameters are setup at the Manager module. The system/application parameters configure the apparatus for its proper operation.

The collector module microphone may comprise a neck band with a microphone mounted in a chamber placed over the supra-sternal notch. However the preferred arrangement as shown in FIG. 1 schematically comprises a wireless microphone inside the ear or by a microphone mounted in a chamber with a neck band to record respiratory sounds followed by a suitable signal conditioning unit depending on the type of the used sensor. The second sensor 21 collects sound from the environment around. The third sensor 22 collects the conventional $SaO_2$ data or other oximetry data. The three sensors allow from the patient simultaneous data acquisition of the sound signals and the $SaO_2$ data.

There are two options for recording respiratory sounds: using the ear microphone or the neck microphone. The very small miniature ear microphone is inserted into a piece of foam which has open ends and inserted to inside the microphone. The small preamplifier of the microphone is placed behind the ear similar to a hearing aid device. The ear microphone includes a wireless transmitter which is placed behind the ear, the miniature microphone and the foam for securing the microphone inside the ear. In case of neck microphone, it is inserted in a chamber (with the size of a loony) which allows about 2 mm distance between the microphone and the skin when the chamber is placed over supra-sternal notch of the trachea of the patient with double sided adhesive ring tapes. The neck microphone will come with a neck band mainly for the comfort of the patient and also to keep the wire of the microphone free of touching the skin. In either case, the preamplifier and transmitter of the wireless microphone can be placed in the pocket of the subject. Alternatively the whole element mounted in the ear canal includes the pre-amplifier and transmitter for complete wireless operation.

Figure 3:
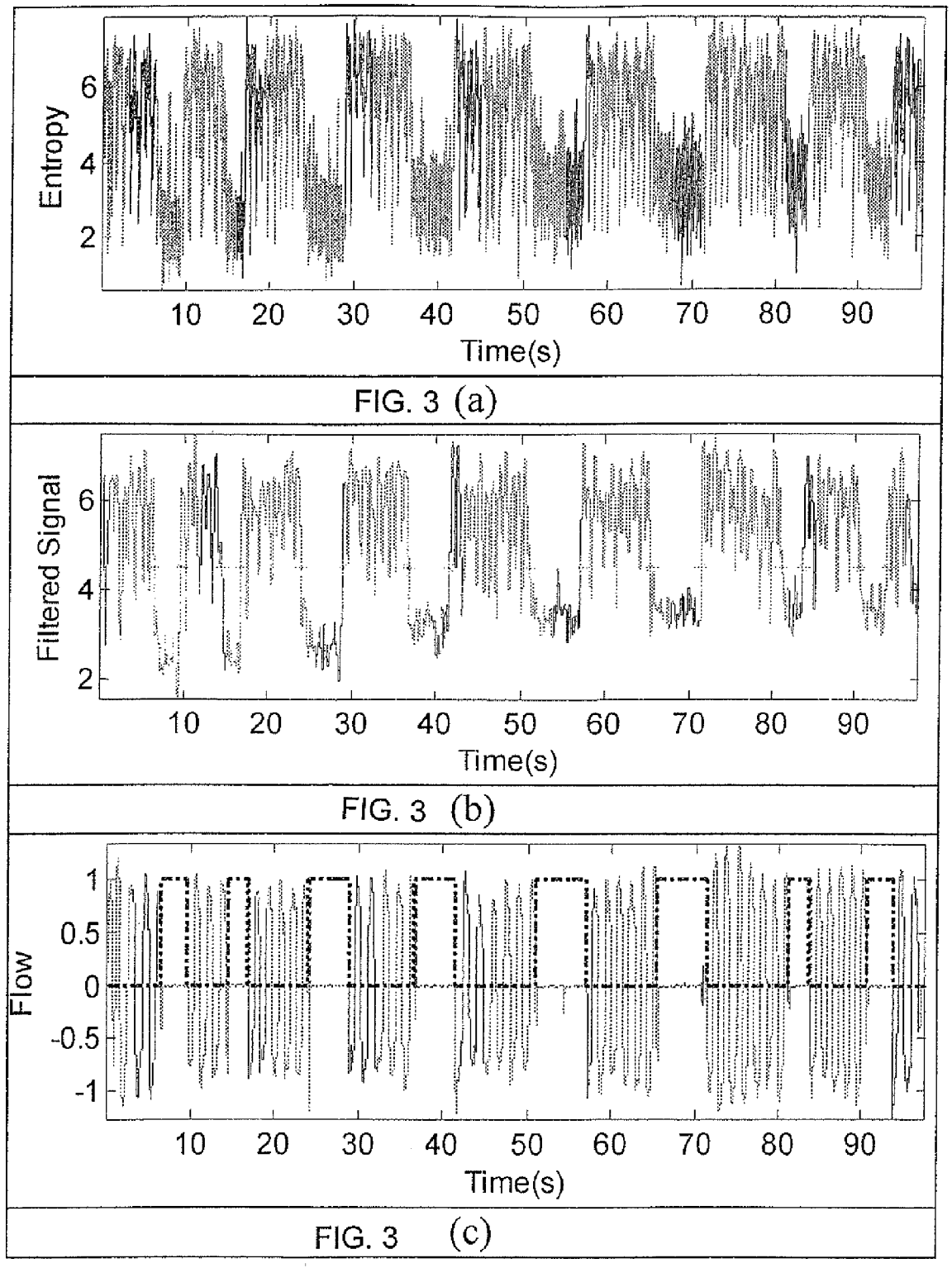
FIG. 3($a$) is a graphical representation of Tracheal sound entropy.

The detector module pre-processes and analyzes the recorded signal in order to provide a user friendly, smart and interactive interface for the physician as a monitoring and diagnostic aid tool. The software in this part will de-noise the recorded sound, separate snoring sounds, estimate the flow acoustically, detect apnea and/or hypopnea episodes, count the duration and the frequency of their occurrence, display the estimated flow with marked apnea episodes as shown in FIG. 3 along with the related information.

The respiratory sounds either from the ear or from the neck of the patient will be recorded by a small wireless microphone. A Transmitter-Sender Module DSP board is designed to receive the analog signal, amplify and filter the signal, digitize it with a minimum of 5120 Hz sampling rate and store it as a binary file.

The $SaO_2$ data simultaneously with the respiratory sounds is digitized with 5120 Hz sampling rate and stored in a binary file for the entire duration of the sleep at the collector module.

The detector module signal processing of the sound signals has three stages. First an automated algorithm finds the artifacts (that normally appear as impulses in the signal) and removes them from further analyses. Secondly, the snoring sounds, if they exist, are identified and separated from the respiratory sounds. Finally, from the cleaned respiratory sounds the entropy of the signal is calculated, the effect of heart sounds is removed, and apnea episodes are detected by the technique as described hereinafter. The average duration of the apnea episodes, their frequency of occurrence and whether they are associated with snoring, is presented as part of the information in the GUI interface for the physician.

Artifacts (usually due to movement) appear as very short duration pulses in the recorded signal. Wavelet analysis is a highly reliable method with high accuracy to automatically detect these artifacts. On the other hand, snoring sounds are musical sounds which appear with harmonic components in the spectrogram of the recorded signal. Detection of snoring sounds is similar to detection of crackle sounds in the lung sounds. Multi-scale product of the wavelet co-efficient is used to detect and separate the snoring sounds. Techniques for the application of digital signal processing techniques on biological signals including noise and adventitious sounds separation are known.

Once the respiratory sound signal is pre-processed and cleaned of extra sounds, the entropy of the signal is calculated. As heart sounds have overlap with respiratory sounds at low frequencies and this is more pronounced at very low flow rate (the case of hypopnea), the effect of heart sounds has to be cancelled from the entropy or the range parameter of the signals prior to apnea detection. This is described in more detail hereinafter.

Then, from the entropy or the range parameter of the signal, the apnea episodes are identified using Otsu's thresholding method as described hereinafter.

The flow estimation method as described hereinafter is enhanced to make the method self-calibrated. That enables the apparatus to estimate the actual amount of flow. Finally, the episodes of hypopnea and apnea are marked; their duration and frequency of occurrence during the entire sleep is presented on the interface module GUI display as a diagnostic aid to the physician.

Depending on the type of microphone used, both sounds result in the same apnea detection episodes and flow estimation while the tuning of the algorithm for each sound signal requires slight modification, i.e. the threshold or the parameters of the flow estimation model are different.

The apnea detection algorithm requires a snoring separation algorithm. This can use one or more of the following principles:

Applying Wavelet analysis to detect and mark the snoring sounds in the time-frequency domain.

Applying the adaptive filter cancellation technique to remove the snoring sounds from the signal using the signal recorded by the auxiliary microphone in the vicinity of the patient.

An automated algorithm can be provided to clean the recorded breath sound signal from all extra plausible noises such as cough sounds, swallowing sounds, vocal noise (in case the patient talks while dreaming), and artifacts due to movements following the apnea detection algorithm on the cleaned signal and validate the results. These extraneous sounds will be removed using wavelet analysis for localization and several different filter banks to remove each type of noises either automatically or at the user's command.

Display

The interface module 14 provides a display of the detected apnea/hypopnea episodes and related information for a clinician. The display includes a display 30 of airflow versus time is plotted with apnea and hypopnea episodes marked on the screen.

The display includes oximetry data 31 plotted in association with the estimated airflow.

The display has touch screen controls 32, 33 providing zoom-in and zoom-out functions in the same window for both airflow and oximetry data simultaneously.

The display is capable of playing the breathing and snoring sounds in any zoomed-in or zoomed-out data window, that is the sounds are stored to allow an actual rendition of those sounds to the clinician to study the sounds at or around an apnea event.

The display is capable of displaying the extracted information about the frequency and duration of apnea/hypopnea episodes, and their association with the level of oximetry data in a separate window for the clinician.

Apnea Detection

Referring now to FIGS. 4(a), 4(b) and 4(c), further detail of the Sleep Apnea detection components is now described.

In order to smooth the calculated entropy or range parameter, it is segmented into windows of 200 ms with 50% overlap between adjacent windows. Each window was then presented by its median value which is not sensitive to jerky fluctuation of the signal.

Next, the smoothed entropy or the smoothed range signal is classified into two groups of breathing and apnea using a nonparametric and unsupervised method for automatic threshold selection using the principles of OTSU.

In Otsu's method the threshold is chosen such that the variance between classes is maximized. The between-class variance is defined as the sum of variances of all classes respect to the total mean value of all classes:

$$\sigma_B^2 = w_0(\mu_0 - \mu_T)^2 + w_i(\mu_i - \mu_T)^2, \quad (1)$$

where $w_i, \mu_i (i=1,2)$ are the probability and mean values of the classes, respectively and $\mu_i$ is the average of total values.

and the optimum threshold $k^*$ is selected so as:

$$\sigma_B^2(k^*) = \max_{1 \leq k < L} \sigma_B^2(k). \quad (2)$$

The average of entropy or range values is another statistical measure that can be used to detect apnea segments. In this study both the Otsu and the average value of entropy or range value were used to define the classification threshold as:

$$\text{Thr} = \min\{k^*, m\} \quad (3)$$

where $k^*$ is the Otsu threshold and m is the average of the entropy or range values.

Figure 4:
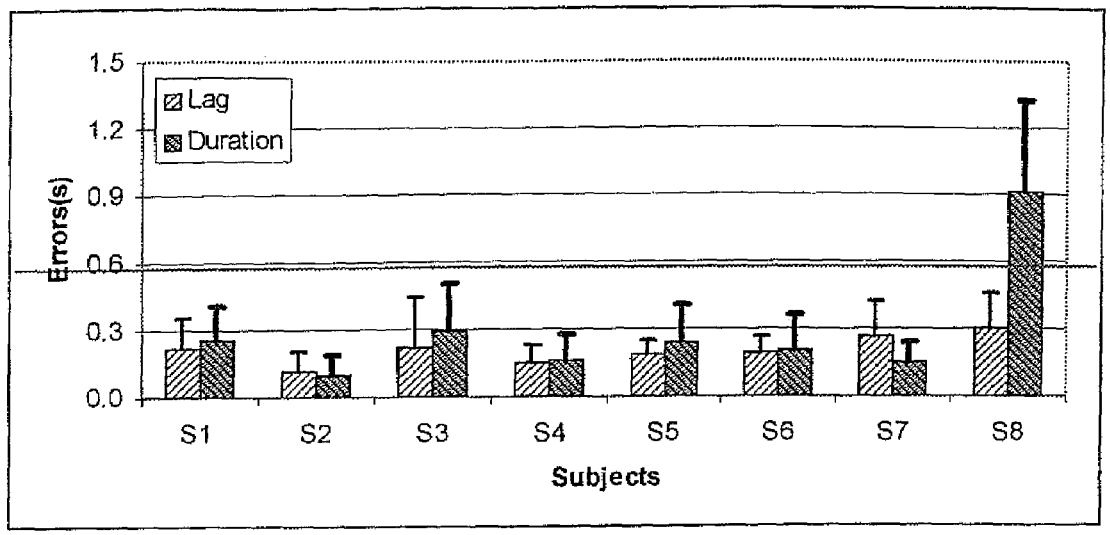
FIG. 4 is a graphical representation of Mean and standard deviation values of errors in estimating apnea periods for different subjects

FIG. 4 presents (a) Tracheal sound entropy, (b) entropy after applying nonlinear median filter (star marks represents the estimated apnea segments) and c) flow signal (solid line) along with the estimated (dotted line) and real (dashed line) apnea segments for a typical subject. Comparing the results depicted in FIG. 4(a) and FIG. 4(b), the effect of applying median filter is evident. The star marks in FIG. 4(b) show the estimated apnea segments. Investigating the results depicted in FIG. 4(c) it is clear that the proposed method detects all the apnea segments and classifies them correctly from the breath segments.

In this arrangement a new acoustical method for apnea detection is proposed which is based on tracheal sound entropy or range value. The method is fast and easy to be implemented, which makes it suitable for on-line applications.

Removal of snoring sounds by time-frequency filtering techniques may have some problems due to the fact that snoring sounds also have strong low frequency components, in which the acoustical apnea detection is based on. As an alternative, the snoring sounds can be recorded by another auxiliary microphone in the vicinity of the subject. This signal will not have breathing sounds and can be used as a noise reference. The apparatus then uses adaptive filtering for noise (snore) cancellation.

Snoring sounds are musical sounds which appear with harmonic components in the spectrogram of the recorded signal. We record the snoring sounds by an auxiliary microphone in the vicinity of the patient. Using the source of noise (recorded by the auxiliary microphone) adaptive filtering will cancel the snoring sounds from the breath and snoring sounds recorded over the neck or inside the ear of the patient.

Figure 5:
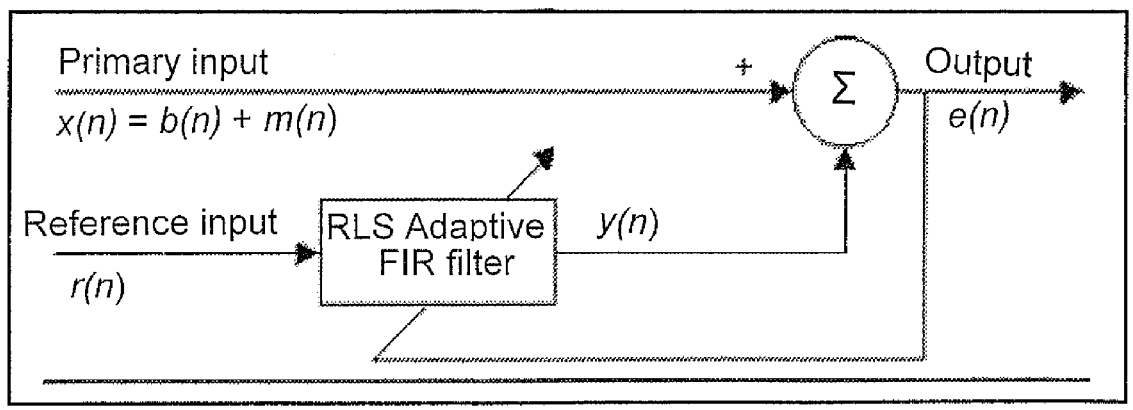
FIG. 5 is a block diagram illustrating the adaptive filtering scheme for removing the snoring sounds from the signal using the signal recorded by the auxiliary microphone in the vicinity of the patient.

FIG. 5 illustrates the block diagram of the adaptive filtering scheme. The filter has two inputs: the primary input and the reference signal. The primary input, x(t), (the microphone over the neck or inside the ear) contains an interference, m(n), (snoring sounds) along with the information bearing signal, b(n), (tracheal sound). The reference input, r(n), (the auxiliary microphone) represents a version of interference with undetectable information bearing (tracheal sounds) signal. The output of the RLS FIR filter, y(n), is close to the interference component of the primary signal. Therefore, the output of the adaptive filter, e(n), is the minimum mean square error estimate of the information bearing signal, $\hat{b}(n)$.

Computational demand of the smart, automated algorithm to run 8 hours of sleep data can be high. As an alternative, the algorithms are written in C++ code that increases the speed of the algorithms compared to a high level signal processing software such as MATLAB. With fast, state-of-art new computers, this will not be a problem considering that this system will replace the 4 hours labor work of an sleep lab technician (the usual time to analyze one PSG patient's data) with a few minutes of processing time.

Flow Estimation

Flow Calibration

In order to provide an effective flow estimation method it is desirable to provide another sound channel recorded over the lung to be used for respiratory phase detection and second it is desirable to provide one breath with known flow from the patient to calibrate (tune) the model to that patient. This calibration (tuning) is necessary because there is a wide variation of flow-sound relationship between the subjects due to their different chest size, lung capacity, gender, age, etc.

Respiratory Phase Detection

Thus the present arrangement provides a method of respiratory phase detection with only one channel breath sound (Tracheal sound signal).

In this method the patient is required to have a deep breath, hold it, start the program and then exhale and keep breathing normally but with different flow rates from low to high for 30 seconds. This 30 second data that starts with expiration phase is used by the program to derive the necessary information for phase detection of the rest of breath sounds. The phase detection algorithm is:

1. Sequester the 30 second initialization data into 100 ms segments with 50% overlap between the successive segments.

2. Calculate the average power (in dB) of each segment over the range of 150-450 Hz. The valleys of the resultant signal, which looks like a rectified sinusoid, determine the onsets of the breaths.

3. Knowing that the first phase is the exhalation, label the initialization data as inspiration/expiration phases. Also by comparing the max power in each phase, label them as low, tidal and high flow rates.

4. Calculate the mean value of the average power (this time calculated over the range of 500-1200 Hz of each segment) of the top 20% of each phase and store it for inspiration and expiration phases separately.

5. Calculate the ratio of the mean of the average power calculated in Step 4 between the inspiration and expiration phases.

6. Apply this ratio as a threshold to the rest of the data to determine respiratory phases. For example, if the ratio of inspiration and expiration is calculated as 1.2, and the ratio of any known phase respect to the adjacent phase (calculated with the same method) is equal to 0.8, it means that the first known phase is expiration and the second one is inspiration.

Automatic Self Calibration

Since having one breath with known flow defeats the purpose of eliminating the flow measurement, in this arrangement is provided a method of automatic self calibration using a data bank. The concept includes a very large data bank of breathing sounds (tracheal sound) of people. This data bank is sorted based on body-mass-index (BMI), age, gender, and smoking history of the subjects. This data is used to match the patient's BMI and other information to suggest the known flow-sound relationship required for calibration.

De-noising and Adventitious Sound Removal

Since the patient might have some respiratory diseases that may cause some adventitious sounds, i.e., crackle sounds or wheezes, an algorithm is required to be run by the choice of the user (the clinician) to remove all adventitious sounds prior to flow estimation.

This algorithm has two parts: adventitious sound localization and removal. For adventitious localization the arrangement herein uses multi-scale (level 3) product of wavelet coefficients and applies a running threshold of mean plus three times of standard deviation to detect and localize the adventitious sounds. Then, the segments including artefacts will be removed in time-frequency domain, the signal will be interpolated by spline interpolation and the breath sound signal will be reconstructed in time domain by taking the inverse of the spectrogram.

Flow Estimation Using Entropy or Range Parameter

1. Band-pass filter the tracheal sounds in the frequency range of 75 to 600 Hz and normalize the signal.

2. Sequester the band-pass filtered signal into segments of 50 ms (512 samples) with 75% overlap between the successive segments.

3. Let x(t) be the signal in each segment. The range value in each segment can be defined as:

$$L_r = \log[\text{mean}(x|x>[\max(x)*(1-r/100)])-\text{mean}(x|x<[\max(x)*r/100])] \quad (1)$$

where x is the tracheal sound signal in each window and mean( ) is the average value, and r=1, or:

$$L_r = \log[\text{var}(x)], \quad (2)$$

where var(x) is the variance of the signal in each segment.

4. The other feature that can be used for flow estimation is the entropy of the signal in each segment. Let $(X_1, \ldots, X_N)$ represent the values of signal x in each segment. Estimate the probability density function (pdf) of signal x(t), p(x), in each window using the Normal kernel estimator:

$$\hat{p}_k(x) = \frac{1}{N}\sum_{i=1}^{N}\frac{1}{h}K\left(\frac{x-X_i}{h}\right), \quad (3)$$

where N is the number of samples (205), K is the Gaussian kernel function $(K(x)=(2\pi)^{-1/2}\exp(-x^2/2))$ and h is the kernel bandwidth. For Gaussian kernel the optimum h is approximated as:

$$h_{opt} = 1.06\hat{\sigma}(x)N^{-0.2} \quad (4)$$

where $\hat{\sigma}(x)$ is the estimated standard deviation of the signal x(t) in each window. Calculate the Shannon entropy in each segment:

$$L_r = -\sum_{i=1}^{N} p_i \log(p_i). \quad (5)$$

5. Use the modified linear model (6) to estimate flow from tracheal sounds entropy or range (Eq. 1, 2 or 5) feature:

$$F_{est} = C_1\left(\frac{\text{mean}(L_{ph})}{\text{mean}(L_{base})}\right)L_{ph} + C_2, \quad (6)$$

where $C_1$ and $C_2$ are the model coefficients derived from the one breath with known flow, $L_{ph}=[L_1, \ldots, L_w]$ is a vector representing the entropy or range value of the signal in the upper 40% values of each respiratory phase (inspiration or expiration), w is the number of segments in the upper 40% values of each respiratory phase and $L_i$ is the entropy or range values of tracheal sound in each segment (Eq. 1, 2 or 5). Similarly, $L_{base}$ is the same vector that is calculated using the base respiratory phase signal. Base respiratory phase is the one breath that is assumed to be available with known flow to calibrate the model.

Heart Sounds Localization

1. Band-pass filter the tracheal sound records in the range of 75-2500 Hz to remove motion artifacts and high-frequency noises.

2. Divide the filtered signal into segments of 20 ms (205 samples) with 50% overlap between successive segments.

3. Let x(t) be the signal in each segment. The range value in each segment can be defined as:

$$L_r = \log[\text{mean}(x|x>[\max(x)*(1-r/100)])-\text{mean}(x|x<[\max(x)*r/100])] \quad (7)$$

where x is the tracheal sound signal in each window and mean( ) is the average value, and r=1, or:

$$L_r = \log[\text{var}(x)], \quad (8)$$

where var(x) is the variance of the signal in each segment.

The other feature that can be used for heart sounds localization is entropy of the signal. Let $\{X_1, \ldots, X_N\}$ represent the values of signal x in each segment. Estimate the probability density function (pdf) of signal x(t), p(x), in each window using the Normal kernel estimator:

$$\hat{p}_k(x) = \frac{1}{N}\sum_{i=1}^{N}\frac{1}{h}K\left(\frac{x-X_i}{h}\right), \quad (9)$$

where N is the number of samples (205), K is the Gaussian kernel function $(K(x)=(2\pi)^{-1/2}\exp(-x^2/2))$ and h is the kernel bandwidth. For Gaussian kernel the optimum h is approximated as:

$$h_{opt} = 1.06\hat{\sigma}(x)N^{-0.2}. \quad (10)$$

where $\hat{\sigma}(x)$ is the estimated standard deviation of the signal x(t) in each window.

4. Calculate the Shannon entropy in each segment:

$$H(p) = -\sum_{i=1}^{N} p_i \log(p_i). \quad (11)$$

5. Define average plus standard deviation value (μ+σ) of the calculated entropy or range value as the threshold for heart sounds localization.

6. Mark the segments with entropy or range values of higher than this threshold as heart sounds-included segments.

Removing the Effects of Heart Sounds

1. Localize heart sounds with the method mentioned above.

2. Calculate the range or entropy values for the segments void of heart sounds.

3. Apply spline interpolation to estimate the values of the entropy or range value in the segments including heart sounds. This technique effectively cancels the effect of heart sounds on the entropy or range values of the tracheal sound.

EXAMPLE 1

Eight healthy subjects (3 males) aged 33.1±6.6 years with body mass index of 23.3±3.5 participated in this study. Tracheal sound was recorded using Siemens accelerometer (EMT25C) placed over supra-sternal notch using double adhesive tapes. Respiratory flow signal was measured by a mouth piece pneumotachograph (Fleisch No.3) connected to a differential pressure transducer (Validyne, Northridge, Calif.). The subjects were instructed to breathe at very shallow flow rates with different periods of breath hold (2, 4, 6 sec) to simulate apnea. Tracheal sound and flow signals were recorded and digitized simultaneously at a 10240 Hz sampling rate.

Feature Extraction

Among several features of tracheal sound such as the sound's mean amplitude, average power and entropy used for flow estimation, entropy and the range of signal have been shown to be the best features following flow variation. Therefore, in this study tracheal sounds entropy was used to detect apnea (breath hold in the experiments of this study) without the use of the measured flow signal. However, the recorded flow signal was used for validation of the acoustically detected apnea.

Tracheal sound signal was band-pass filtered in the range of [75-600] Hz, and then segmented into 50 ms (512 samples) windows with 50% overlap between the adjacent windows. In each window the tracheal sound probability density function (pdf) was estimated based on kernel methods. Then, using the method described earlier in this document Shannon entropy was calculated in each window that represents the changes in the signal's pdf. The effect of heart sounds which is most evident in the frequency range below 200 Hz was removed by the method introduced earlier in this document.

FIG. 3 shows the calculated entropy and its corresponding flow signal for a typical subject. By comparing the signals depicted in FIG. 1(a) and FIG. 1(c) (solid line), it is evident that the values of entropy in the breath hold segments are smaller than those during breathing.

It should be noted that when localizing the segments including heart sounds, it is nearly impossible to find out the exact boundaries of heart sounds segments. Therefore, there is always a trade off between the amount of heart sounds interference in respiratory sounds and the amount of respiratory sounds information missing during heart sounds cancellation. The high peaks in the calculated entropy (FIG. 3a) are related to the heart sounds components remained in the tracheal sound. FIG. 4 displays the mean and standard deviation values of length and lag errors in estimating apnea periods for different subjects.

EXAMPLE 2

In this study 10 healthy subjects of the previous participated. Subjects were in two age groups: 5 adults (all female) 29±8 years old and 5 children (3 female) 9.6±1.7 years old. Respiratory sounds were recorded using Siemens accelerometers (EMT25C) placed over supra-sternal notch and the upper right lobe lung. Respiratory flow was measured by a pneumotachograph (Fleisch No.3) connected to a differential pressure transducer (Validyne, Northridge, Calif.). Subjects were instructed to breathe at 5 different flow rates with 5 breaths at each target flow followed by a 10 s of breath hold at the end of experiment. In this study the shallow (<6 ml/s/kg), low (6-9 ml/s/kg), medium (12-18 ml/s/kg), high (18-27 ml/s/kg) and very high (>27 ml/s/kg) target flow rates were investigated. Tracheal sound signals were used for flow estimation while the lung sound signal in correspondence with tracheal sound signal were used for respiratory phase detection. The onsets of breaths were detected by running a threshold on the average power of the tracheal sounds and detecting the valleys of the signal. Since lung sounds are much louder during inspiration as opposed to expiration, then by comparing the average power of the lung and tracheal breath sounds it can easily and accurately be determined which phases are inspiration or expiration.

As described above, the best performance for estimating flow from tracheal sound entropy was achieved in the frequency range of 75-600 Hz. Tracheal sound signals were used for flow estimation while the lung sound signal in correspondence with tracheal sound signal were used for respiratory phase detection as mentioned above.

As described above, the best performance for estimating flow from tracheal sound entropy was achieved in the frequency range of [75 600] Hz. This is in accordance with the fact that the main energy components of tracheal sound exists in the frequency range below 600-800 Hz. Thus, tracheal sound was band-pass filtered in this range followed by segmenting the band-pass filtered signal into segments of 50 ms (512 samples) with 75% overlap between the successive segments.

When studying tracheal sound in the frequency range below 300 Hz, heart sounds are the main source of interference that changes the time and frequency characteristics of the tracheal sound. Therefore, the presence of heart sounds will cause an error which can become significant in flow estimation in very shallow breathing, when most of the signal's energy is concentrated at low frequencies. Hence, in this study the effect of heart sounds on the extracted parameters was cancelled by using the same method as described above.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. Apparatus for use in analysis of breathing of a patient during sleep for detection of apnea comprising:
   a microphone arranged to be located on the patient for detecting breathing sounds;
   a transmitter at the patient for transmitting signals from the breathing sounds to a remote location;
   a detector module for receiving and analyzing the signals to extract data relating to the breathing;
   the detector module being arranged to analyze the signals to generate an estimate of air flow while extracting extraneous sounds related to snoring or heart;
   the detector module being arranged to analyze the estimate of air flow to detect periods of apnea or hypopnea;
   and a display of the detected apnea or hypopnea episodes and related information for a clinician;
   wherein the detector module is arranged to generate an estimate of air flow during breathing by calculating a function representing the range of the signals which is defined as the log of the difference between minimum and maximum of the signal within each window of data.

2. The apparatus according to claim 1 wherein
   the microphone is arranged so as to be attached on the neck of the patient so as to receive sounds in the neck emanating from the breathing of the patient.

3. The apparatus according to claim 1 wherein there is provided a second microphone to collect extraneous sounds from the patient and a sensor for oximetric signals for transmission to the remote receiver.

4. The apparatus according to claim 1 wherein there is provided a second microphone arranged to receive sounds from the patient in the vicinity of the patient so as to be sensitive to snoring and wherein the detector module is arranged to use adaptive filtering to extract the signals relating to the snoring from the signals including both the breathing sounds and the snoring sounds.

5. The apparatus according to claim 1 wherein sleep apnea or hypopnea is detected by comparing the function to a threshold.

6. The apparatus according to claim 5 wherein the threshold is defined as the minimum of the Otsu's threshold and the average value of the function within each data window.

7. The apparatus according to claim 6 wherein the Otsu's threshold is defined as the threshold which maximizes the between class variance.

8. The apparatus according to claim 5 wherein the display includes a display of airflow versus time is plotted with apnea and hypopnea episodes marked in.

9. The apparatus according to claim 8
wherein the display includes oximetry data plotted in association with the estimated airflow.

10. The apparatus according to claim 9 wherein the display is capable of zoom-in and zoom-out functions in the same window for both airflow and oximetry data simultaneously.

11. The apparatus according to claim 9 wherein the display is capable of playing the breathing and snoring sounds in any zoomed-in or zoomed-out data window.

12. The apparatus according to claim 9 wherein the display is capable of displaying the extracted information about the frequency and duration of apnea or hypopnea episodes, and their association with the level of oximetry data in a separate window for the clinician.

13. The apparatus according to claim 1
wherein the microphone is arranged to be located in the ear of the patient so as to receive sounds emanating from the breathing of the patient and wherein the microphone in the ear includes a transmitter arranged for wireless transmission to a receiver.

14. Apparatus for use in analysis of breathing of a patient during sleep for detection of apnea comprising:
a microphone arranged to be located on the patient for detecting breathing sounds;
a transmitter at the patient for transmitting signals from the breathing sounds to a remote location;
a detector module for receiving and analyzing the signals to extract data relating to the breathing;
the detector module being arranged to analyze the signals, while extracting extraneous sounds related to snoring or heart, to detect periods of apnea and/or hypopnea;
and a display of the detected apnea or hypopnea episodes and related information for a clinician;
wherein the detector module is arranged to generate an estimate of air flow during breathing by calculating a function representing the entropy of the signals where entropy is defined by the following formula:

$$H(p) = -\sum_{i=1}^{N} p_i \log p_i,$$

where $p_i$ is the probability distribution function of the $i^{th}$ event.

15. The apparatus according to claim 14 wherein the microphone is arranged so as to be attached on the neck of the patient so as to receive sounds in the neck emanating from the breathing of the patient.

16. The apparatus according to claim 14 wherein there is provided a second microphone to collect extraneous sounds from the patient and a sensor for oximetric signals for transmission to the remote receiver.

17. The apparatus according to claim 14 wherein there is provided a second microphone arranged to receive sounds from the patient in the vicinity of the patient so as to be sensitive to snoring and wherein the detector module is arranged to use adaptive filtering to extract the signals relating to the snoring from the signals including both the breathing sounds and the snoring sounds.

18. The apparatus according to claim 14 wherein the display includes a display of airflow versus time is plotted with apnea and hypopnea episodes marked in.

19. The apparatus according to claim 14 wherein the display includes oximetry data plotted in association with the estimated airflow.

20. The apparatus according to claim 14 wherein the display is capable of zoom-in and zoom-out functions in the same window for both airflow and oximetry data simultaneously.

21. The apparatus according to claim 14 wherein the display is capable of playing the breathing and snoring sounds in any zoomed-in or zoomed-out data window.

22. The apparatus according to claim 14 wherein the display is capable of displaying the extracted information about the frequency and duration of apnea or hypopnea episodes, and their association with the level of oximetry data in a separate window for the clinician.

23. The apparatus according to claim 14 wherein the microphone is arranged to be located in the ear of the patient so as to receive sounds emanating from the breathing of the patient and wherein the microphone in the ear includes a transmitter arranged for wireless transmission to a receiver.

* * * * *